(12) United States Patent
Malak

(10) Patent No.: US 8,285,391 B2
(45) Date of Patent: Oct. 9, 2012

(54) HYGIENIC-THERAPEUTIC CONDUCTIVE FAR-INFRARED DEVICES

(75) Inventor: Henryk Malak, Ellicott City, MD (US)

(73) Assignee: American Environmental Systems, Inc., Ellicott City, MD (US)

( * ) Notice: Subject to any disclaimer, the term of this patent is extended or adjusted under 35 U.S.C. 154(b) by 1731 days.

(21) Appl. No.: 11/598,265

(22) Filed: Nov. 13, 2006

(65) Prior Publication Data

US 2008/0077203 A1    Mar. 27, 2008

Related U.S. Application Data

(60) Provisional application No. 60/846,879, filed on Sep. 25, 2006.

(51) Int. Cl.
*A61F 7/00* (2006.01)
(52) U.S. Cl. .......................... 607/100; 607/98
(58) Field of Classification Search .............. 607/96, 607/100, 98; 250/504; 392/407, 435; 219/553, 219/545; 237/46; 601/19, 20
See application file for complete search history.

(56) References Cited

U.S. PATENT DOCUMENTS

| | | | | |
|---|---|---|---|---|
| 5,459,327 A * | 10/1995 | Nomura | | 250/504 R |
| 6,057,532 A * | 5/2000 | Dexter et al. | | 219/553 |
| 6,575,379 B1 * | 6/2003 | Wang | | 237/46 |
| 6,591,141 B2 * | 7/2003 | Lee | | 607/98 |
| 2002/0077679 A1 * | 6/2002 | Lo | | 607/90 |
| 2003/0155347 A1 * | 8/2003 | Oh et al. | | 219/545 |
| 2006/0226378 A1 * | 10/2006 | Yabiku | | 250/504 R |
| 2006/0263074 A1 * | 11/2006 | Xing | | 392/407 |
| 2007/0172215 A1 * | 7/2007 | Chang | | 392/435 |
| 2008/0292293 A1 * | 11/2008 | Song, II | | 392/347 |

FOREIGN PATENT DOCUMENTS

| | | | | |
|---|---|---|---|---|
| JP | 02000079153 A | * | 3/2000 | |
| JP | 02002220746 A | * | 8/2002 | |

* cited by examiner

*Primary Examiner* — Roy Gibson

(57) ABSTRACT

This invention relates to novel hygienic-therapeutic or personal care devices that are based upon intense far-infrared sources in which radiation is generated by novel conductive materials. The conductive materials are specially designed and made to radiate ten to thousands times more intense far-infrared radiation than typical conductive materials, and such strong far-infrared radiation is achieved with high, typically greater than 90%, conversion efficiency of energy to radiation. The radiation properties of the proposed conductive materials do not follow the Wien's law ("black body" law). The devices are intended to be used in therapy, medicine, cosmetic technology, hygiene technology, or household use.

4 Claims, 5 Drawing Sheets

HYGIENIC-THERAPEUTIC CONDUCTIVE FAR-INFRARED DEVICES

CROSS REFERENCE TO RELATED PATENT APPLICATION

This application claims the benefit of U.S. Provisional Application Ser. No. 60/846,879 filed Sep. 25, 2006, entitled "Conductive Far-Infrared Devices", which is incorporated by reference.

FIELD OF THE INVENTION

This invention is generally related to hygienic, therapeutic, and medical care methods, devices, and applications.

BACKGROUND OF THE INVENTION

The medical benefits of far-infrared radiation on the living body have been known for a long time, and therefore, there are far-infrared devices on the market for improving human and animal health. Most of these devices produce far-infrared radiation by using ceramic materials. In order to generate far-infrared radiation at intensities suitable for therapy or sterilization, the ceramic materials must be heated to high temperatures, sometimes few hundred degrees C. This limits the use of existing far-infrared devices in many hygienic-therapeutic applications, for example, using them for dental oral care or hair care to kill bacteria and microbes, and to rejuvenate teeth, gums and hair. In addition, the generation of far-infrared radiation in these devices is not energy-efficient; efficiencies typically are only a few percent or less. Therefore, there exists a strong need for hygienic-therapeutic far-infrared devices which will produce intense far-infrared radiation with high efficiency, and would operate at relatively low temperatures.

The devices with ceramic far-infrared radiation sources might also cause some health problems. Most of the ceramics are made from powder or clay and during their use, the ceramic materials can chip off (erode) from the surface and can be inhaled by the living body. Therefore, there is a great need for intense infrared radiation sources that are more environmentally safe and do not expose humans or animals to health risks.

Another limitation of the devices with ceramic far-infrared radiation sources is fixed radiation spectra which cannot be changed to increase the effectiveness of therapy. The living body is most influenced by infrared radiation within the wavelength range of 8 to 12 microns and many currently used devices cannot deliver radiation at this spectral range.

To mitigate the previously stated issues of using ceramics as far-infrared sources in hygienic-therapeutic devices, this invention proposes to use novel conductive sources emitting intense far-infrared radiation with a high conversion efficiency of energy to radiation, typically greater than 90%. In nature, conductive materials follow the "black body" radiation phenomenon and they do not emit intense far-infrared radiation. However, there are some conductive materials, like carbon fiber and other materials proposed in this invention, which emit very intense far-infrared radiation with extremely high conversion efficiencies of energy to radiation.

SUMMARY OF THE INVENTION

The invention discloses novel hygienic-therapeutic or personal care devices that are based upon intense far-infrared sources where radiation is generated by novel conductive materials. The proposed conductive materials do not follow the Wien's law ("black body" law), i.e. the materials in a wide range of temperatures have a few orders of magnitude more intense infrared radiation than typical conductive materials. In addition, the far-infrared sources generate radiation with very high efficiency, typically greater than 90%.

The scope of the invention includes, for example, far-infrared hygienic-therapeutic/personal care devices selected from the group consisting of: toothbrush, hairbrush, hair dryer, hair straightener, comb, elastic bandage, pad, pain-reliever device, body massager, hygienic therapeutic illuminator, and other far-infrared hygienic-therapeutic/personal care devices.

DESCRIPTION OF PREFERRED EMBODIMENTS

All patents, patent applications, and literature cited or referenced in this description are incorporated herein by reference in their entireties. In the case of inconsistencies, the present disclosure, including definitions and usage, will control.

Figure 1:
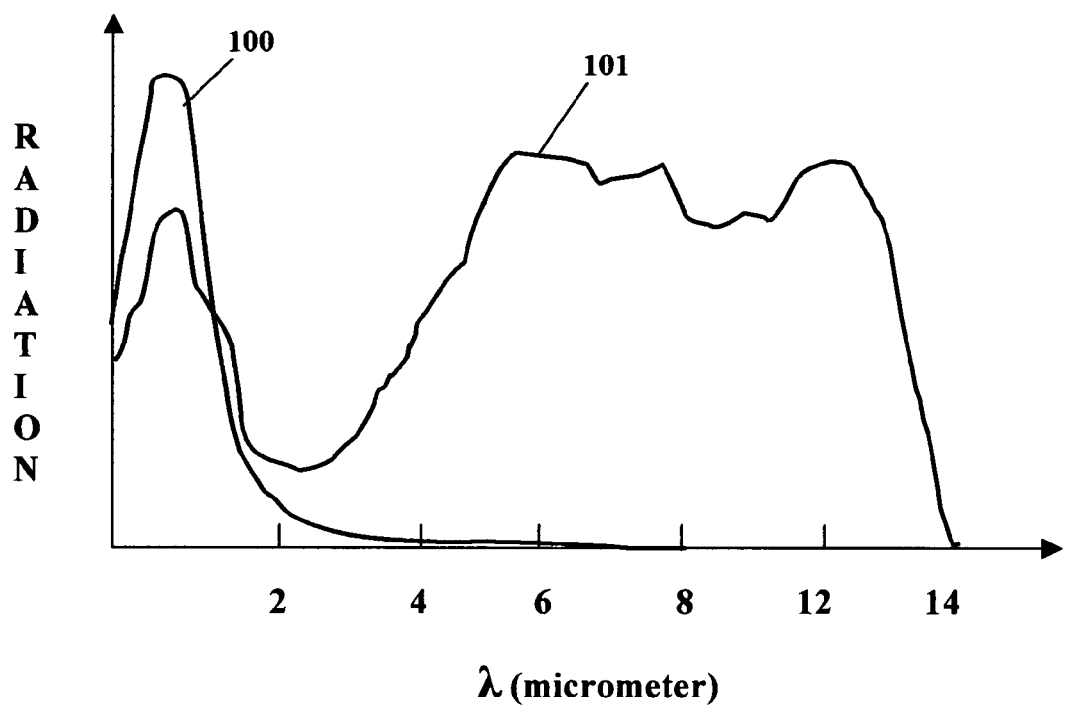
FIG. 1 illustrates "black body" spectra of a typical conductor and a spectrum of a proposed carbon fiber conductor.
Figure 2:
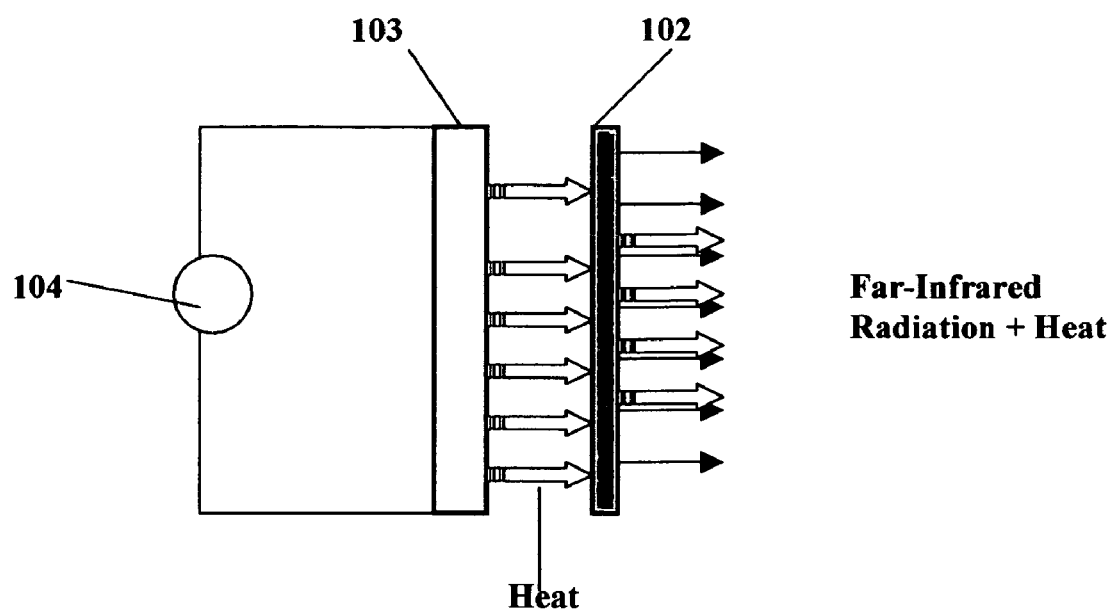
FIG. 2 illustrates a typical arrangement for far-infrared radiation by a ceramic far-infrared source which is heated by a conductor.

The disclosure generally describes novel hygienic-therapeutic or personal care devices that are based upon intense far-infrared sources in which radiation is generated by novel conductive materials 101. The conductive materials are specially designed and made to radiate ten to thousands times stronger far-infrared radiation than typical conductive materials 100, and such strong far-infrared radiation is achieved with high, typically greater than 90%, conversion efficiency of energy to radiation. The radiation properties of the proposed conductive materials do not follow the Wien's law ("black body" law) as is shown in FIG. 1. The proposed far-infrared sources can be made, for example, from a commercially available carbon fiber conductive material 101 that emits very intense far-infrared radiation with close to 98% conversion efficiency of electric energy to radiation and at wavelengths within 2 microns to 14 microns as is shown in FIG. 1. Radiation at these wavelengths is well absorbed by human or animal bodies and as well such radiation also kills effectively bacteria and microbes, therefore this radiation can be successfully used for hygienic and therapeutic purposes. The disclosed devices with the intense far-infrared sources are superior to existing far-infrared devices that are based upon dielectric/ceramic sources 102 in which far-infrared radiation is much less intense, conversion efficiency of energy to radiation is only a few percent or less due to using electric heater 103 to heat up dielectric/ceramic sources 102 (FIG. 2), the spectral radiation properties of dielectric/ceramic sources are fixed, and their temperatures are very high limiting their use in many hygienic-therapeutic applications.

Figure 5:
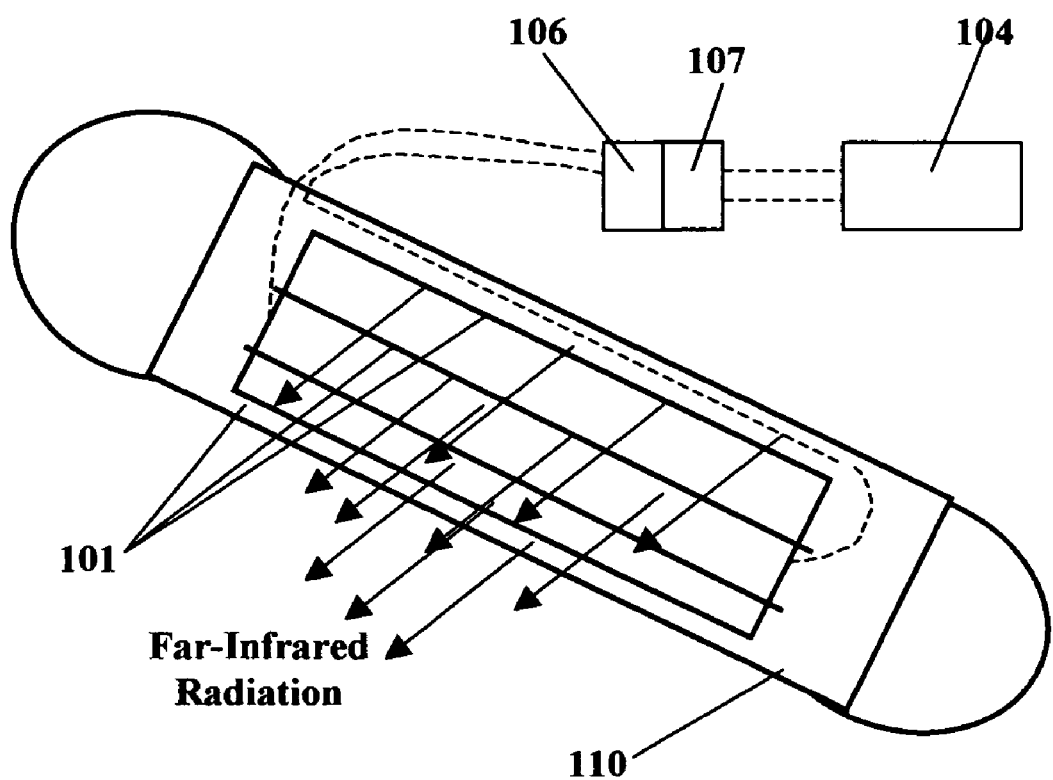
FIG. 5 illustrates an elastic bandage in accordance with an embodiment of the present invention.

It should be understood that the figures illustrate certain components (i.e., conductive source 101, dielectric-ceramic source 102, electric heater 103, power supply 104) as contained within housing 110. In alternative embodiments, however, these components maybe partially or wholly external to the particular devices. For example electronics 106, a computer or processor 107 and a power supply 104 maybe partially or wholly external to the housing 110 on the bandage as illustrated in FIG. 5. It should also be noted that the housing may comprise of a unitary structure or multiple structures.

Figure 3:
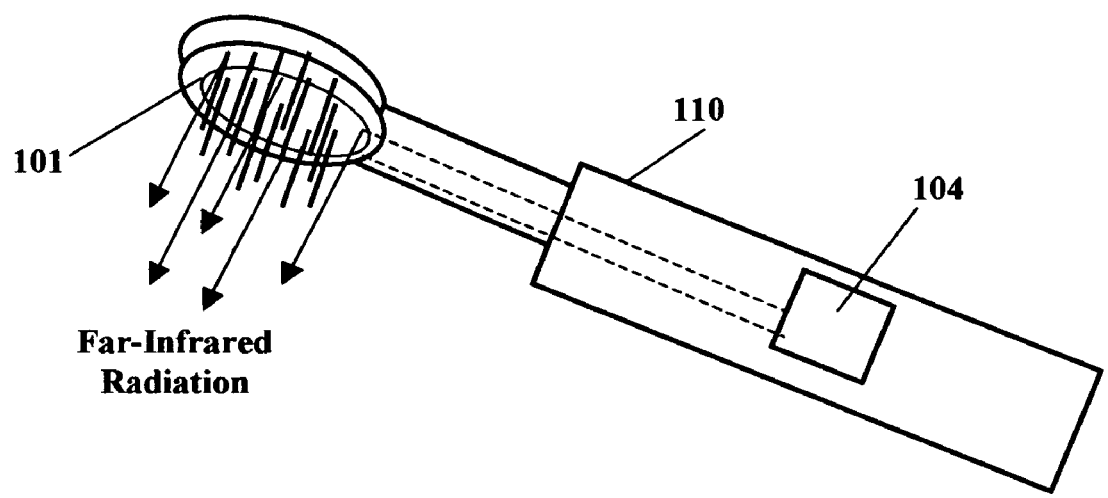
FIG. 3 illustrates a toothbrush in accordance with an embodiment of the present invention.
Figure 4:
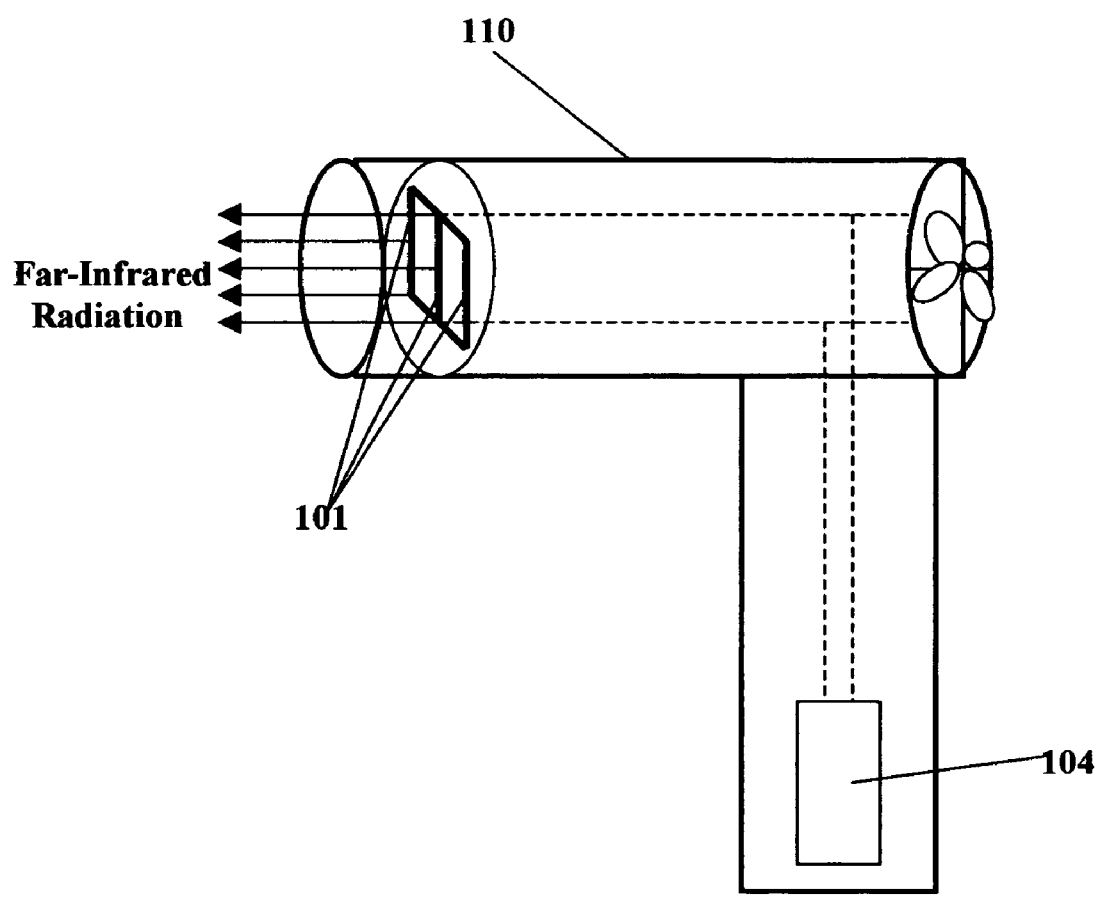
FIG. 4 illustrates a hair dryer in accordance with an embodiment of the present invention.

The scope of the invention includes, for example, far-infrared hygienic-therapeutic/personal care devices selected from the group consisting of: toothbrush, hairbrush, hair dryer, hair straightener, comb, elastic bandage, pad, pain-reliever device, body massager, hygienic therapeutic illuminator, and other far-infrared hygienic-therapeutic/personal care devices. Examples of the devices are illustrated in FIGS. 3-5.

In an embodiment, the invention considers the use of the novel conductive materials which emit high intensity far-infrared radiation. The conductive material, for example, a carbon fiber made as a wire 101, is placed in a toothbrush head and connected to a toothbrush battery 104 as is shown in FIG. 3. The strong far-infrared radiation emitted by the wire in the toothbrush is used for dental oral care. The wire may be covered with the dielectric/ceramic material 102 or may be embedded into an infrared transparent plastic to alter the spectral properties of the far-infrared radiation source 101 or to convert wavelengths of the far-infrared radiation source into to wavelengths that are more suitable for use in hygienic-therapeutic applications. The proposed far-infrared toothbrush is a novel hygienic-therapeutic device that provides, for dental oral care, two additional non-invasive functions: sterilization and rejuvenation of teeth and gums. Another example of the proposed device is a hair dryer shown in FIG. 4. In the proposed hair dryer, electric heating wires are made of the far-infrared conductive material 101 that is emitting high intensity far-infrared radiation with the high-efficiency conversion of electricity to radiation, typically greater than 90%. Therefore, the proposed hair dryer may consume less electric energy in addition to lower electrical consumption due to a much faster hair drying time using far-infrared radiation. So, it is expected that the proposed hair dryer will use only 50% or less of the electric energy that is used by the regular hair dryers. In addition, hair drying will be less damaging to hair, and more hygienic and therapeutical. The intense far-infrared emitted by the hair dryer can also be successfully used for killing microbes, microbe eggs/spores in hair and scalp, and as well for healing skin diseases, like for example, psoriasis. Therefore, the hair dryer can also be qualified as a medical device. Another example of the device is an elastic bandage that is shown in FIG. 5. The far-infrared conductive material 101 is embedded into a textile material 110 and connected to power supply 104, electronics 106 and/or computer 107. When current passes through the elastic bandage, it generates strong far-infrared radiation and residual heat which are used for hygienic-therapeutic purposes. Please note that arrangements/designs of the far-infrared source in the devices show in FIGS. 3-5 are only examples, therefore the invention is not limited to these arrangements/designs.

The scope of the invention includes far-infrared sources made of the novel conductive materials selected from the group of: super conductive, conductive, or semiconductive. These materials emit far-infrared radiation at intensities much higher, usually ten to thousands times higher, than is predicted by the Wien's law ("black body" law). In addition, these materials produce this radiation with very high efficiency.

Another embodiment of the invention considers delivering electric energy to the radiation source 101 in different modes: DC (direct current), AC (alternative current), frequency, or pulse. The use of the single mode or the plurality modes in the device allows tuning the far-infrared radiation of the device according to body properties and hygienic-therapeutic needs.

Although the invention has been explained in relation to its preferred embodiment as mentioned above, it is to be understood that many other possible modifications and variations can be made without departing from the scope of the present invention. It is, therefore, contemplated that the appended claim or claims will cover such modifications and variations that fall within the true scope of the invention.

What is claimed is:

1. A far-infrared hygienic-therapeutic device selected from the group of a hair dryer, a hairbrush, a hair straightener, a comb, a toothbrush, a body massager or an elastic bandage comprising: a far-infrared conductor, wherein the conductor is being able to radiate far-infrared radiation and heat; a heat retardation cover placed on the far-infrared conductor, wherein the heat retardation cover retards heat radiated by the far-infrared conductor; and an electric power supply, wherein the electric power supply is connected to the far-infrared conductor; and wherein the far-infrared conductor is a carbon fiber conductor.

2. The device of claim 1, wherein the electric power supply delivers electric energy to the far-infrared conductor in a single mode or a plurality modes selected from the group consisting of: DC, AC, frequency, or pulsed.

3. The device of claim 2, wherein the single mode or the plurality modes changes hygienic-therapeutic properties of the device.

4. The device of claim 1, wherein the heat retardation cover is further capable of changing far-infrared radiation properties of the far-infrared conductor for hygienic-therapeutic purposes.

* * * * *